United States Patent [19]

Kraus

[11] Patent Number: 5,475,131

[45] Date of Patent: Dec. 12, 1995

[54] PROCESS FOR THE PREPARATION OF A MIXTURE OF AMINOMETHYLENATED GLUTACONIC ACID DINITRILES

[75] Inventor: Helmut Kraus, Odenthal, Germany

[73] Assignee: Bayer Aktiengesellschaft, Leverkusen, Germany

[21] Appl. No.: 351,992

[22] Filed: Dec. 8, 1994

Related U.S. Application Data

[63] Continuation-in-part of Ser. No. 180,945, Jan. 12, 1994.

[30] Foreign Application Priority Data

Jan. 19, 1993 [DE] Germany .......................... 43 01 238.8

[51] Int. Cl.⁶ .................................................. C07C 253/30
[52] U.S. Cl. ........................... 558/457; 558/360; 558/361; 558/377
[58] Field of Search ..................... 558/361, 377, 558/457

[56] References Cited

U.S. PATENT DOCUMENTS

| | | | |
|---|---|---|---|
| 3,138,631 | 6/1964 | Frazza et al. | 260/465 |
| 4,849,432 | 2/1989 | Shiokawa et al. | 514/341 |
| 4,849,519 | 7/1989 | Maurer | 546/298 |

FOREIGN PATENT DOCUMENTS

| | | |
|---|---|---|
| 0000483 | 2/1979 | European Pat. Off. . |
| 0162464 | 11/1985 | European Pat. Off. . |

OTHER PUBLICATIONS

Scotti, et al.; J. Org. Chem. 29 (1964), pp. 1800–1808.
Sasaki, et al.; J. Chem. Soc. 1969 (c), pp. 1086–1088.

*Primary Examiner*—Joseph Paul Brust
*Attorney, Agent, or Firm*—Sprung Horn Kramer & Woods

[57] ABSTRACT

Aminomethylenated glutaconic acid dinitriles of the formula

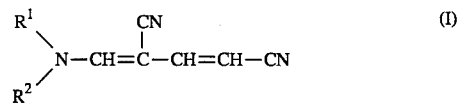

(I)

in which $R^1$ and $R^2$ independently of one another represent hydrogen, straight-chain or branched $C_1$–$C_8$-alkyl, $C_3$–$C_8$-alkenyl, $C_2$–$C_8$-alkoxyalkyl, $C_4$–$C_8$-alkoxyalkenyl, $C_3$–$C_8$-cycloalkyl, $C_6$–$C_{12}$-aryl, $C_7$–$C_{10}$-aralkyl or a 5- to 8-membered, saturated or unsaturated heterocyclic ring containing 1 or 2 heteroatoms from the group comprising N, O and S, are obtained by reacting 3-amino-acrylonitriles of the formula

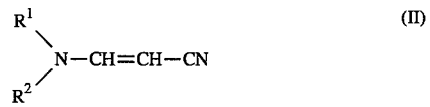

(II)

in which the radicals $R^1$ and $R^2$ have the meaning mentioned, with one another at from 0° to 100° C. in the presence of at least 0.5 equivalents of an acidic compound.

7 Claims, No Drawings

PROCESS FOR THE PREPARATION OF A MIXTURE OF AMINOMETHYLENATED GLUTACONIC ACID DINITRILES

This application is a continuation-in-part application of parent application Ser. No. 180,945, filed Jan. 12, 1994.

The invention relates to a process for the preparation of 5-amino-4-cyano-penta-2,4-dienenitriles (aminomethylenated glutaconic acid dinitriles) by dimerization of the 3-amino-acrylonitriles on which they are based, the title compounds being obtained in the form of mixtures when starting from 3-amino-acrylonitriles with different substitution.

The compounds which can be prepared in accordance with the claims are important intermediates for the preparation of heterocycles. A particularly elegant reaction is the ring closure to give 2,5-disubstituted pyridines, which are required for the production of herbicides (EP 483) or insecticides (EP 235 725). In principle, 5-amino-4-cyano-penta-2,4-dienenitriles should be able to be prepared, by analogy with EP 268 964, by reacting glutaconic acid dinitrile with o-amides. However, glutaconic acid derivatives can only be prepared by complex methods; industrial processes are not at present known.

In EP 162 464 a $C_6$-pyridine precursor is synthesized from a $C_3$-enamine and α-chloroacrylonitrile. When using identical $C_3$-amines, however, the $C_6$ formation, i.e. the desired dimerization, is only an intermediate step in the direction of more extensive—and unwanted—formation of oligomers and/or polymers; the intermediate step cannot be controlled and can therefore not be exploited industrially.

J. Org. Chem. 29 (1964), 1800 describes a dimerization of dimethylaminoacrylonitrile in the presence of glacial acetic acid. However, the yield of 40% of theory leaves much to be desired.

The dimerization of 3-dimethylamino-acrylonitrile in the presence of sulphuric acid provides a still inadequate 51% of the theoretical yield if the reaction is interrupted after 4 minutes and the mixture worked up (dissertation by M. Saur, Univ. of Stuttgart 1971). In industry, however, a reaction regime of this type can only be carried out with very great complexity and in uneconomically small batches.

It was therefore surprising that it was possible to discover a process which permits 5-amino-4-cyanopenta-2,4-dienenitriles to be prepared by selective dimerization of the correspondingly substituted acrylonitriles on which they are based. A feature of the process according to the invention is the high purity of the reaction products, which are obtained in more than 90% of the theoretical yield. On the other hand, follow-on reactions are avoided, so that it is possible to isolate and work up the products as normal, for example by filtration through a suction filter.

The invention accordingly relates to a process for the preparation of a mixture of aminomethylenated glutaconic acid dinitriles of the formula

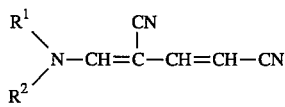

in which

R$^1$ and R$^2$ independently of one another represent hydrogen, straight-chain or branched $C_1$–$C_8$-alkyl, $C_3$–$C_8$-alkenyl, $C_2$–$C_8$-alkoxyalkyl, $C_4$–$C_8$-alkoxyalkenyl, $C_3$–$C_8$-cycloalkyl or unsaturated heterocyclic ring containing to 8-membered, saturated or unsaturated heterocyclic ring containing 1 or 2 heteroatoms from the group comprising N, O and S, which is characterized in that 3-amino-acrylonitrile of the formula

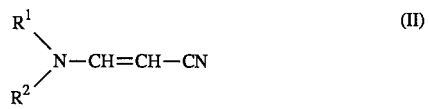

in which

R$^1$ and R$^2$ have the scope of meaning mentioned, are reacted with one another at from 0° to 100° C. in the presence of at least 0.5 equivalents, preferably from 0.5 to 50 equivalents of an acidic compound per mole of the total quantity of 3-amino-acrylonitrile. The reaction is preferably carried out in a non-aqueous system, i.e. in the absence of water.

If 3-amino-acrylonitriles with different substitution (i.e. mixtures of 3-aminoacrylonitriles with, for example, two different NR$^1$R$^2$ substituents) are used for the dimerization by the process according to the invention, both the amines HNR$^1$R$^2$ are removed as elimination products in a reaction which is in principle of equal status. Accordingly, the mixture of reaction products obtained in accordance with the invention may contain in the region of 50 mol % of each of the two substances I. However, if there is a marked difference in the substituents NR$^1$R$^2$, one of the two elimination amines may predominate. For instance it is observed that, when aromatic groups are present in the context of the scope of meaning of R$^1$ and R$^2$, these aromatic groups are also found in the reaction product, while the non-aromatic groups are eliminated in the form of the amine. The reaction products of the formula (I) can be separated from their mixtures by fractional distillation, crystallization, chromatography and other methods.

The process according to the invention can also be carried out in the presence of an additional amine of the formula

in which

R$^3$ and R$^4$ have the meaning indicated above for R$^1$ and R$^2$.

In case of this type, amine exchange is always observed between the starting material (II) and the amine (III), so that reaction product of the formula (I) can be obtained in a sufficient quantity.

This particular embodiment of the invention can, for example, be used in cases where the starting compounds are difficult to prepare.

However, in many cases the aim will be to avoid mixtures of the reaction products (I) which require an additional separation. In such a case the starting materials employed are those in which the NR$^1$R$^2$ substituents are identical. In other words, the only starting material employed is one of the formula (II) and the only reaction product obtained is one of the formula (I).

Straight-chain or branched $C_1$–$C_8$-alkyl is for example methyl, ethyl, propyl, isopropyl, butyl, isobutyl, tert-butyl, the isomeric pentyls, hexyls and octyls, preferably the $C_1$–$C_4$-alkyl radicals mentioned.

Straight-chain or branched $C_3$–$C_8$-alkenyl denotes for example the isomeric butenyls, pentenyls, hexenyls or octenyls, preferably the $C_3$–$C_4$-alkenyl radicals mentioned.

Straight-chain or branched $C_2$–$C_8$-alkoxyalkyl is for example methoxymethyl, ethoxymethyl and further radicals from the group $C_3$–$C_9$-alkyl in which a $CH_2$ group is replaced by an O atom.

Straight-chain or branched $C_4$–$C_8$-alkoxyalkenyl is for example methoxyallyl, 2-methoxy-propenyl and other from the group $C_4$–$C_9$-alkenyl in which a $CH_2$ group is replaced by an O atom.

$C_3$–$C_8$-cycloalkyl is for example cyclopropyl, methylcyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl, cyclopentyl and cyclohexyl, and methyl or dimethyl derivatives thereof.

$C_6$–$C_{12}$-aryl is for example phenyl, naphthyl or biphenylyl, preferably phenyl.

$C_7$–$C_{10}$-aralkyl is for example benzyl, 1-phenylethyl, 2-phenylethyl and further radicals of this type which are known to those skilled in the art, preferably benzyl.

As a 5- to 8-membered, saturated or unsaturated heterocyclic ring containing 1 or 2 heteroatoms from the group comprising N, O and S, the following may be mentioned: pyrrole, furan, thiophene, pyrrolidine, pyrazole, imidazole, thiazole, oxazole, pyridine, pyrimidine, piperazine which can be substituted on the N atom by $C_1$–$C_4$-alkyl or by hydroxy-$C_1$–$C_4$-alkyl, morpholine, pyran, azepin, azocine, isoxazole, isothiazole, pyridazine and pyrazine. It is known to those skilled in the art that unsaturated heterocyclic rings may have a more or less pronounced aromatic character. Preferred such saturated or unsaturated heterocyclic rings which may be mentioned are morpholine, pyrrolidine and piperidine, which may be substituted by $C_1$–$C_4$-alkyl or by hydroxy-$C_1$–$C_4$-alkyl.

The substituted β-amino-acrylonitriles required as starting materials are readily accessible by reaction of salts of formylpropiononitrile with secondary amines (EP 18 473) or by condensation of o-amides with acetonitrile.

The reaction according to the invention is carried out at a temperature of from 0° to 100° C., preferably from 10° to 80° C., most preferably from 10° to 60° C.

The reaction according to the invention is, furthermore, carried out in the presence of preferably from 0.5 to 50 equivalents, more preferably from 1 to 10 equivalents, of an acidic compound per mole of the total quantity of starting materials of the formula (II).

The process according to the invention can be represented in terms of formulae, in the preferred form in which the $NR^1R^2$ substituents are identical, as follows:

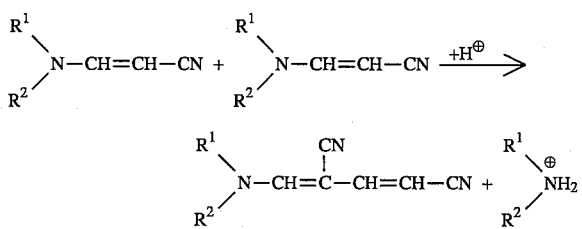

Acidic compounds which may be employed in accordance with the invention are organic and inorganic acids and their adducts with polar organic compounds. It is preferred to employ organic acids or adducts of inorganic acids with polar organic compounds.

Preferred examples of polar organic compounds comprise dimethylformamide (DMF), dimethylacetamide, dimethylsulfoxide, N-methylpyrrolidone, N-methylcaprolactam, tetramethyl urea, acetonitrile and acetone.

Examples of adducts of inorganic acids with polar organic compounds are DMF/HCl, DMF/$H_2SO_4$, acetonitrile/HCl, dimethylacetamide/HCl and acetone/HCl. Among these adducts, some are stable only in solution; however, it is preferred to employ the adducts which can be isolated as substances.

Suitable organic acids are in particular aliphatic $C_1$–$C_6$-carboxylic acids and their halogeno or $C_1$–$C_4$-alkoxy derivatives. Examples of such acids are formic acid, acetic acid, propionic acid, butyric acid, dichloroacetic acid, methoxyacetic acid and substances of analogous construction which are well known to those skilled in the art. These acids are preferably employed as anhydrous substances. In order to ensure the absence of water, it is possible to add a small quantity of the corresponding N-phenylpyridone.

The process according to the invention can be carried out with or without organic diluent. In the case where an organic diluent is used, suitable such diluents are those from the group comprising hydrocarbons, halogenated hydrocarbons, ketones, amides, nitriles, ethers and esters. Examples are toluene, xylene, chlorobenzene, ligroin, acetone, methyl ethyl ketone, acetonitrile, chloroform, methylene chloride, dichloroethane, ethyl acetate, butyl acetate, methyl tert-butyl ether, tert-amyl methyl ether, dimethylformamide (DMF), N-methylpyrrolidone (NMP), N-methylcaprolactam (NMC), tetramethylurea and other substances well known to those skilled in the art.

In the case where the acidic compound employed is, preferably, an aliphatic $C_1$–$C_6$-carboxylic acid or a halogeno or alkoxy derivative thereof, such acids can also be used as the reaction medium, so that it is possible to dispense with an additional diluent. In this case the acids are employed in an amount which is within the upper part of the abovementioned range.

As mentioned in the introduction to the description, the glutaconic acid dinitriles prepared in accordance with the invention are suitable for the ring closure to give 2,5-disubstituted pyridines. The reaction medium for the process according to the invention (acidic compound and organic diluent or organic acid without a diluent) is therefore advantageously chosen such that this cyclization can be carried out immediately therein. Examples are DMF/HCl and DMF/$H_2SO_4$. In a further advantageous variant, the reaction medium is chosen such that the glutaconic acid dinitrile is formed therein in the form of a suspension which can still be stirred with ease, and can be isolated easily after the end of the reaction. An isolation of this type involves filtering off the precipitated reaction product with suction, concentrating to a large extent the mother liquor which is formed, and washing the residue with water. During this process, further reaction product is precipitated in a similarly high purity. However, it is just as suitable to concentrate the crude reaction mixture completely and to add water, the reaction product again being obtained in solid form.

As regards the reaction regime and the yield, it is not critical whether the starting materials are pure trans-aminoalkylnitrile or mixtures which on account of their preparation contain a proportion of the cis isomer.

For the preparation of aminomethylenated glutaconic acid dinitriles with predetermined amine substituents, it is possible on the one hand to use the correspondingly substituted amino-acrylonitrile. The industrially prepared 3-dimethylamino-acrylonitrile is to be reacted in the manner described above with the desired amine of the formula (III). The use of aniline in this variant leads, for example, to 5-phenylamino-4-cyano-penta-2,4-diene nitrile, a precursor for the corresponding N-phenylpyridone.

The percentage in the following Examples refer to percentages by weight.

EXAMPLES

Example 1

192 g of 99.5% 3-dimethylaminoacrylonitrile (contains 0.3% DMF; 98.2% trans and 1.8% cis compound) were pumped into 2 l of glacial acetic acid. It was necessary to maintain the batch for the first 15 minutes at room temperature, by gentle cooling. After being stirred for 17 h the solution was concentrated on a rotary evaporator at 14 mbar and at a bottom temperature of 50° C. The residue was stirred together with 1.3 l of water, the solid was filtered off with suction and washed with 200 ml of water. After it had been dried at 50° C. (300 mbar), 129.3 g of a pale orange powder were obtained, corresponding to 88.4% of the theoretical yield. The mother liquor was extracted with methylene chloride and concentrated; a further 4.2% of product were obtained.

N,N-Dimethylaminomethylene-glutaconic acid dinitrile: m.p.: 121°–122° C. $^1$H-NMR (d-DMSO): 3.2 ppm, d (J=28 Hz), 6 H; 4.95 ppm, d (J=15 Hz), 1H; 7.18 ppm, 1(J=15 Hz), 1H; 7.47 ppm, s, 1H.

Example 2

3 mol of 3-dimethylaminoacrylonitrile (92% trans, 8% cis) were dimerized in 1620 ml of glacial acetic acid. The suspension was concentrated, water was added to the residue, and the solid was filtered off with suction. 199.2 g of 98.9% pure product were obtained, corresponding to 89.3% of the theoretical yield. The mother liquor contained a further 3.6% of product.

Example 3

9.6 g of 3-dimethylaminoacrylonitrile were added dropwise to 30 ml of glacial acetic acid, the mixture was stirred for 14 h and the suspension was filtered off with suction. 5.4 g of yellow solid were obtained, corresponding to 73.5% of the theoretical yield. After concentration of the mother liquor and addition of water, it was possible to isolate a further 1.3 g, corresponding to a total yield of 91.2%.

Example 4

By analogy with Example 3, 0.1 mol of 3-dimethylaminoacrylonitrile was added dropwise to a mixture of 54 ml of glacial acetic acid and 5 ml of acetic anhydride. 2.3 g of orange acicular crystals were obtained, as were 4.5 g of orange powder after concentration and addition of water. The concentrated mother liquor (4.5 g) contained 3.4% of dimer, i.e. 92.5% isolated yield or 94.7% overall yield. As a by-product in 1.1% of the theoretical yield, 1,3,5-tricyanobenzene was identified.

Example 5

9.6 g of 3-dimethylaminoacrylonitrile and 9.3 g of aniline were added dropwise to 50 ml of glacial acetic acid. The temperature rose during this to 40° C. The mixture was left to stand overnight and the orange suspension was filtered with suction. 6.8 g of 5-phenyl-aminomethylene-glutaconic acid dinitrile were obtained, corresponding to 69.7% of the theoretical yield.

$^1$H-NMR (d-DMSO): 5.23 ppm (d, 16 Hz, 1H); 7.08 to 7.43 ppm (m, 6H); 8.25 ppm (d, 16 Hz, 1H); 10.55 ppm (d, 14 Hz, 1H).

Example 6

9.6 g of 3-dimethylaminoacrylonitrile were added dropwise to a solution of 11 g of DMF/HCl adduct in 50 ml of DMF. The temperature was initially maintained at 30° C. by gentle cooling. After being stirred for 5 h at room temperature, the pale yellow suspension was concentrated, 20 ml of water were added, and the solid was filtered off with suction. 6.55 g of 96.2% pure product were obtained, corresponding to 91.0% of the theoretical yield.

Example 7

A solution of 28.8 g of 3-dimethylaminoacrylonitrile in 180 ml of glacial acetic acid was heated at 50° C. for 2 hours and was then concentrated in vacuo at this temperature. After addition of water and work-up, the product was obtained in a yield of 87% of theory.

I claim:

1. Process for the preparation of an aminomethylenated glutaconic acid dinitrile of the formula

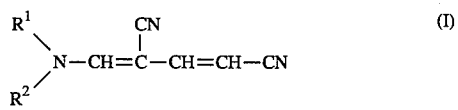

in which

R$^1$ and R$^2$ independently of one another represent hydrogen, straight-chain of branched C$_1$–C$_8$-alkyl, C$_3$–C$_8$-alkenyl, C$_3$–C$_8$-alkoxy-alkyl, C$_4$–C$_8$-alkoxyalkenyl, C$_3$–C$_8$-cycloalkyl, C$_6$–C$_{12}$-aryl or C$_7$–C$_{10}$-aralkyl, characterized in that at least one 3-amino-acrylonitrile of the formula

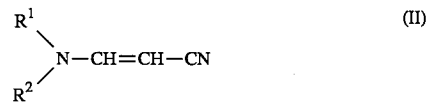

in which

R$^1$ and R$^2$ have the scope of meaning mentioned, is reacted at from 0° to 100° C. in the presence of at least 0.5 equivalent of an acidic compound per mole of the total quantity of 3-amino-acrylonitrile, the overall yield of I being at least 69.7% when R$^1$ and R$^2$ are both methyl.

2. Process according to claim 1, characterized in that an additional amine of the formula

is employed in which R$^3$ and R$^4$ have the scope of meaning given in claim 1 for R$^1$ and R$^2$.

3. Process according to claim 1, characterized in that the acidic compounds employed are organic acids.

4. Process according to claim 3, characterized in that the acids employed are aliphatic $C_1$–$C_6$-carboxylic acids and their halogeno or $C_1$–$C_4$-alkoxy derivatives.

5. Process according to claim 1, characterized in that the acidic compounds employed are adducts of polar organic compounds and inorganic acids.

6. Process according to claim 1, characterized in that at least 1 equivalent of the acidic compound is employed.

7. Process according to claim 1, characterized in that the reaction is carried out at from 10° to 80° C.

* * * * *